US00PP36866P2

(12) United States Plant Patent
Roberts et al.

(10) Patent No.: US PP36,866 P2
(45) Date of Patent: Jul. 29, 2025

(54) *VIBURNUM* PLANT NAMED 'Bailvibone'

(50) Latin Name: ***Viburnum* hybrid**
Varietal Denomination: Bailvibone

(71) Applicant: Bailey Nurseries Inc., Newport, MN (US)

(72) Inventors: David Jonathan Roberts, Athens, GA (US); Oren McBee, Bishop, GA (US); Justin Schulze, Athens, GA (US)

(73) Assignee: BAILEY NURSERIES, Newport, MN (US)

( * ) Notice: Subject to any disclaimer, the term of this patent is extended or adjusted under 35 U.S.C. 154(b) by 0 days.

(21) Appl. No.: 18/827,722

(22) Filed: Sep. 7, 2024

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
CPC ... A01H 5/02; A01H 5/12; A01H 5/00; A01H 6/00
See application file for complete search history.

(56) References Cited

U.S. PATENT DOCUMENTS

PP28,958 P2 * 2/2018 Dirr ..... Plt./226

* cited by examiner

*Primary Examiner* — June Hwu
(74) *Attorney, Agent, or Firm* — Penny J. Aguirre

(57) ABSTRACT

A new cultivar of *Viburnum* plant named 'Bailvibone' that is characterized by its upright plant habit, its floriferous blooming habit with sweet scented flowers, its ease of rooting and fast finishing from a rooted liner, and its foliage that is thick, semi-evergreen and dark green in color.

3 Drawing Sheets

Botanical classification: *Viburnum* hybrid.
Variety denomination: 'Bailvibone'.

BACKGROUND OF THE INVENTION

The present invention relates to a new and distinct cultivar of *Viburnum* of hybrid origin, botanically known as *Viburnum* 'Bailvibone' and is hereinafter referred to by its cultivar name 'Bailvibone'. 'Bailvibone' represents a new cultivar of deciduous shrub grown for use as an ornamental landscape plant.

The new cultivar is the result of a controlled breeding program conducted by the Inventors in Watkinsville, Georgia. The goal of the breeding program was to develop a new cultivar of *Viburnum* with evergreen foliage and fragrant flowers.

The new cultivar arose from a cross made by the Inventors in Watkinsville, Georgia in spring of 2015 between *Viburnum plicatum* f. *plicatum* 'PIIVIB-I' (U.S. Plant Pat. No. 23,385) as the female parent and *Viburnum* x *burkwoodii* 'Mohawk' (not patented) as the male parent. The Inventor selected 'Bailvibone' as a single unique plant amongst the seedlings that resulted from the above cross in summer of 2016.

Asexual propagation of the new cultivar was first accomplished by one of the Inventors using softwood stem cuttings in summer of 2018 in Winterville, Georgia. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailvibone' as a unique cultivar of *Viburnum*.

1. 'Bailvibone' exhibits an upright plant habit.
2. 'Bailvibone' exhibits a floriferous blooming habit with sweet scented flowers.
3. 'Bailvibone' exhibits easy rooting and fast finishing from a rooted liner.
4. 'Bailvibone' exhibits foliage that is thick, semi-evergreen and dark green in color.

The female parent of 'Bailvibone' differs from 'Bailvibone' in having leaves that are more evergreen and more contorted in shape, a rounded plant form, and a later blooming season. The male parent of 'Bailvibone' differs from 'Bailvibone' in having a deciduous plant habit, a later blooming season, a less productive rooting habit, and a stronger flower fragrance. 'Bailvibone' can be most closely compared to *Viburnum plicatum* f. *plicatum* cultivar 'PIIVIB-II' (U.S. Plant Pat. No. 28,958). 'PIIVIB-II' is similar to 'Bailvibone' in having terminal cymes of white flowers and foliage that is dark green in color. 'PIIVIB-II' differs from 'Bailvibone' in having fainter flower fragrance and leaves that are ovate in shape that turn red-purple in color in fall and winter.

BRIEF DESCRIPTION OF THE DRAWINGS

The accompanying color photographs illustrate the overall appearance and distinct characteristics of the new cultivar. The plant in the photographs is 2.5 years in age as grown in a 2-gallon container in Cottage Grove, Minnesota.

The photograph in FIG. 1 provides a side view of 'Bailvibone' in bloom.

Figure 1:
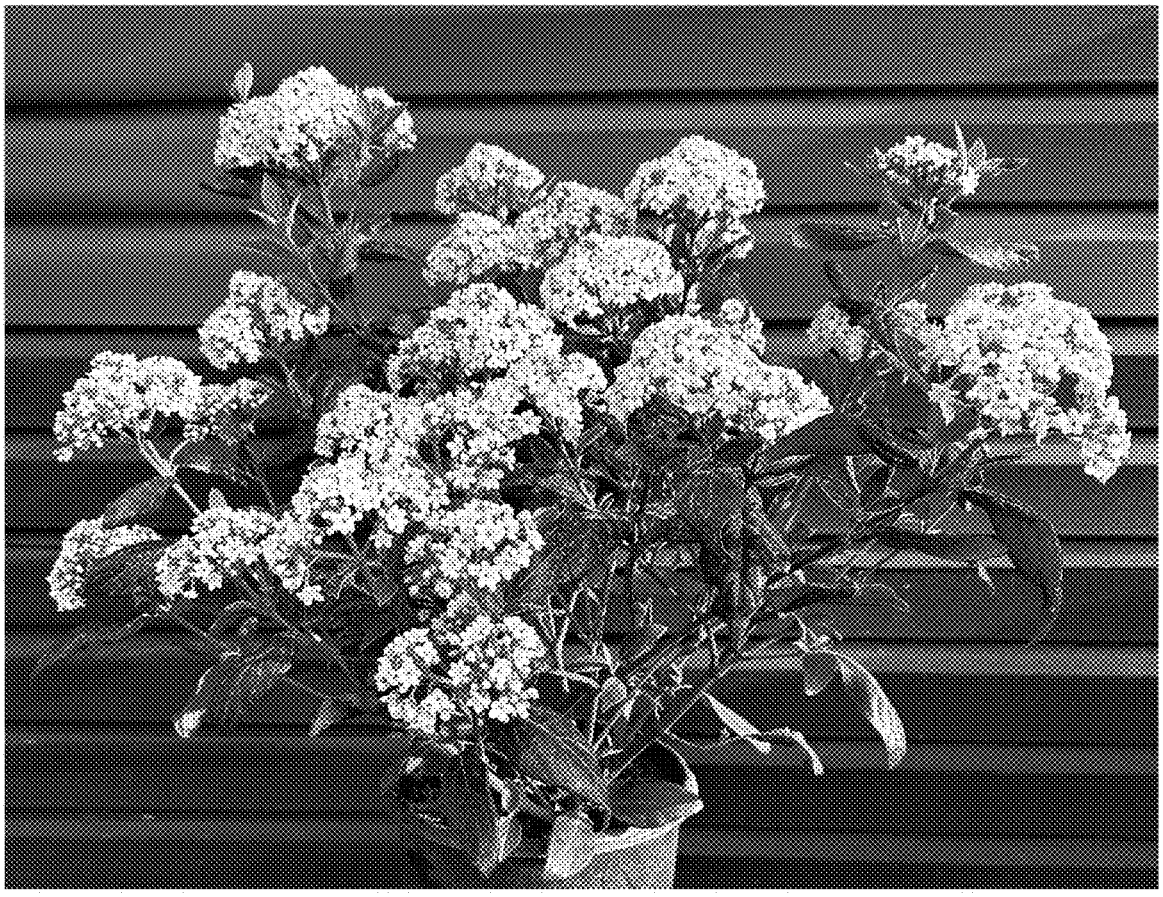
Figure 2:
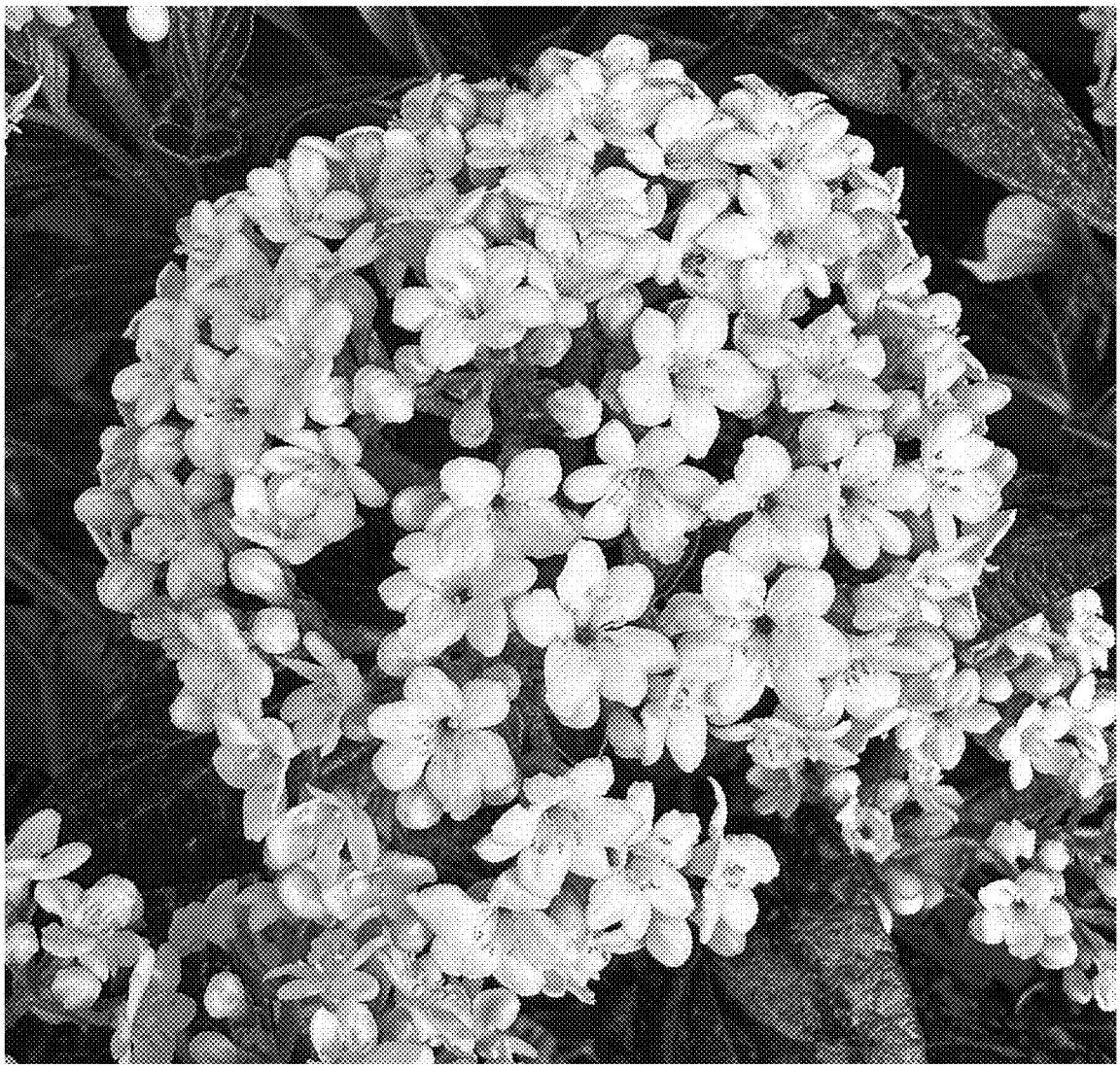

The photograph in FIG. 2 provides a close-up view of an inflorescence of 'Bailvibone'.

Figure 3:
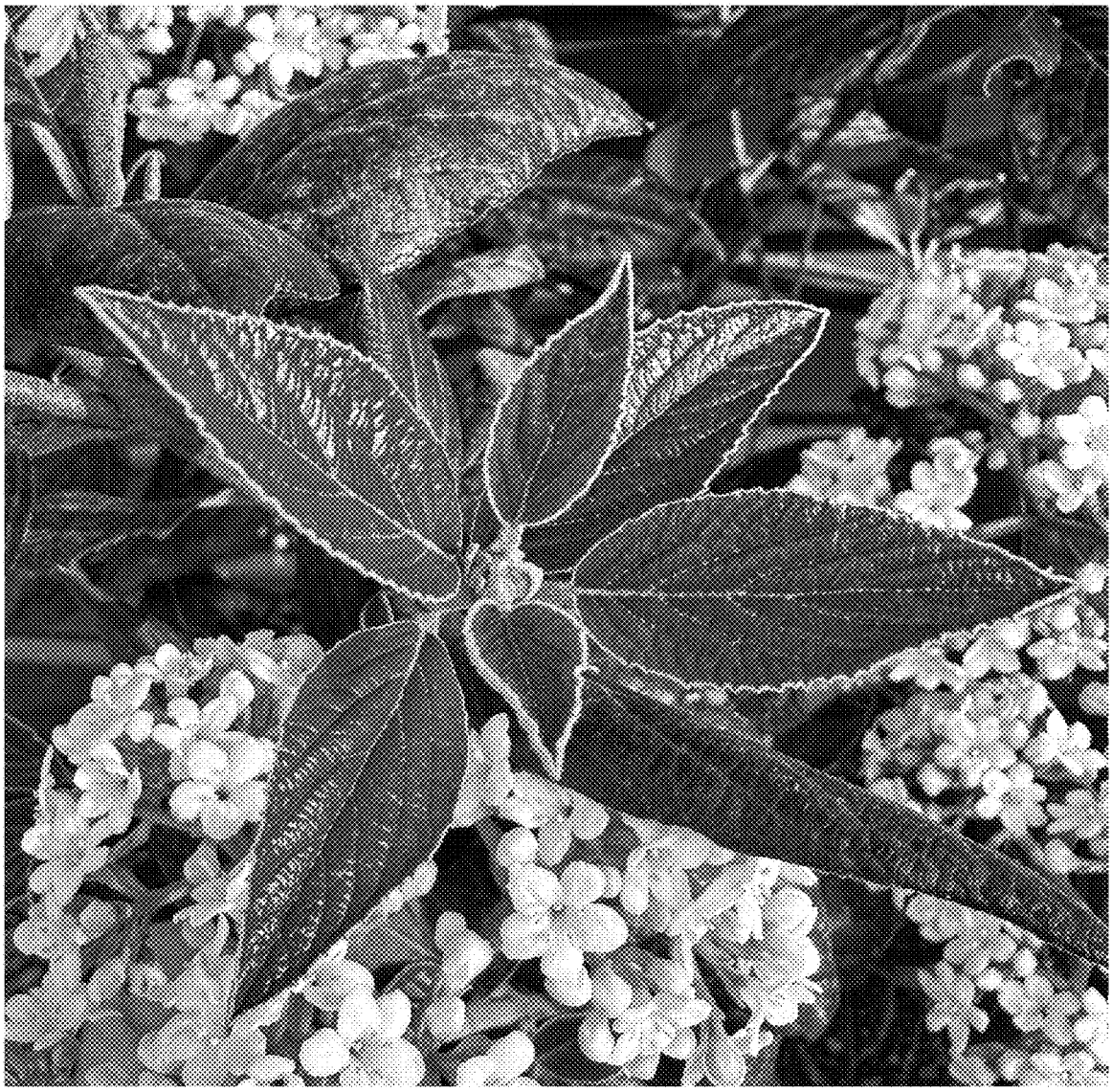

The photograph in FIG. 3 provides a close-up view of the foliage of 'Bailvibone'.

The colors in the photograph may differ slightly from the color values cited in the detailed botanical description, which accurately describe the colors of the new *Viburnum*.

DETAILED BOTANICAL DESCRIPTION

The following is a detailed description of 2.5-year-old plants of the new cultivar as grown in a 2-gallon container in Cottage Grove, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—2 weeks in March in Watkinsville, Georgia.

*Plant type.*—Semi-evergreen shrub.

*Plant habit.*—Compact, upright.

*Plant size.*—56 cm in height and 72 cm in width as a 2-year-old plant as grown in a container, up to 2.4 m in height and 2.1 m in spread as a mature plant in the landscape.

*Cold hardiness.*—At least in U.S.D.A. Zone 6.

*Diseases and pests.*—No susceptibility or resistance to diseases or pests has been observed.

*Root description.*—Numerous, fleshy, well branched and 155A in color.

*Root development.*—Time required for root initiation is about 4 weeks, time required to produce a young plant from rooted cutting is 60 days.

*Propagation.*—Softwood stem cuttings.

*Growth rate.*—Moderate.

Branch description:

*Branch shape.*—Round.

*Branch color.*—Young; 152A, densely covered with tomentose pubescence 162B, mature; striations of N199B and 199B, bark and old wood; a blend of 196A, 199A, and N199B.

*Branch size.*—Main; 5 cm in length, 2.5 cm in diameter, lateral; 43 cm in length, 1.5 cm in diameter, tertiary; 12 cm in length, 1 cm in diameter.

*Branch surface.*—Young; matte and soft to touch due to pubescence coverage, mature; matte and bark-like, bark and old wood; matte slightly exfoliating.

*Branch strength.*—Strong.

*Branching.*—Average of 10 lateral branches, freely branching.

*Internode size.*—Average of 5 cm.

Foliage description:

*Leaf shape.*—Lanceolate to elliptic.

*Leaf division.*—Single.

*Leaf base.*—Broad cuneate.

*Leaf apex.*—Acute.

*Leaf fragrance.*—None.

*Leaf venation.*—Reticulate, young upper surface matches leaf surface, moderately covered with bristly pubescence, 160B in color, 0.5 mm in length, young lower surface; densely covered with tomentose pubescence, 199D in color, mature upper surface; matches leaf surface except main vein 150A in color, mature lower surface; densely covered with tomentose pubescence, 144C in color.

*Leaf margins.*—Entire, slightly undulate and curled downward.

*Leaf arrangement.*—Opposite.

*Leaf attachment.*—Petiolate.

*Leaf surface.*—Young upper surface; slightly glossy, sparsely covered with short bristly pubescence, 160B in color, 0.5 mm in length, young lower surface; matte and densely covered with tomentose pubescence, 195B in color, mature upper surface; glossy, glabrous, slightly rugose and leathery, mature lower surface; matte and densely covered with tomentose pubescence, 144A in color.

*Leaf size.*—An average of 11 cm in length and 4.5 cm in width.

*Leaf quantity.*—An average of 28 per lateral branch.

*Leaf color.*—Young upper surface; 137A and 144A, young lower surface; with pubescence removed 144A, mature upper surface; 147A, lightly flushed with 203A, mature lower surface; with pubescence removed 147A, fall; none, mature leaf color on both surfaces is retained until freeze.

*Petioles.*—Average of 1.5 cm in length and 3 mm in diameter, slightly flattened in shape, densely covered with tomentose pubescence, upper surface 199A to 199B, lower surface 144B.

Flower description:

*Inflorescence type.*—Terminal cyme.

*Lastingness of inflorescence.*—Average of 2 weeks with individual flowers lasting about 1 week.

*Inflorescence size.*—Average of 7 cm in height and 11 cm in diameter.

*Inflorescence number.*—One per lateral stem.

*Flower number.*—An average of 150 flowers per inflorescence.

*Flower fragrance.*—Moderately fragrant, pleasant smell.

*Flower aspect.*—Upright and slightly outward.

*Flower size.*—An average of 1.2 cm in diameter and 1 cm in depth.

*Flower buds.*—An average of 5 mm in length, 3 mm in diameter, oblong in shape, surface is glabrous and glossy, color: emerging buds; 149A, developing buds; 145A, mature buds before burst; NN155A and NN155D, occasionally lightly flushed at the center with 186B.

*Peduncles.*—Moderately strong in strength, flexible, average of 2 cm in length and 2 mm in width, 143B in color, moderately covered with tomentose pubescence, 158C in color, held at various angles to stem.

*Pedicels.*—Moderately strong in strength, flexible, average of 2 cm in length and 2 mm in width, 143B in color, lightly covered with tomentose pubescence, 158C in color, held at various angles to peduncle.

*Petals.*—5 in a single whorl, 40% of base fused, elliptic to slightly obtuse in shape, margins are entire and very slightly undulate, obtuse to rounded apex, both surfaces glabrous and slightly glossy, 7 mm in length, 5 mm width, color: upper surface when opening and fully open; NN155A.

*Bracts.*—1 to 2 at base of pedicel, lanceolate in shape, entire margins, slightly cup-shaped, acute apex and base, both surfaces matte and densely covered with tomentose pubescence, 158C, flushed with N170B, color: upper surface when opening and fully open; pubescence removed 158A.

*Sepals*.—5, 85% fused to base of flower, acute apex, both surfaces glabrous and glossy, 1 mm in length and 0.5 mm in width, inner and outer surfaces 141B in color.

Reproductive organs:

*Stamens*.—5, anthers; 1 mm in length, club-shaped, color; N199C, fading to 202A, filaments; 50% fused to petal, NN155D in color, translucent, surface is glabrous and glossy, 5 mm in length, 1 mm in diameter, pollen; moderate in quantity, 11A in color.

Pistils.—None observed, ovary present; round in shape, superior, 141A, flushed with 187A.

*Seed and fruit*.—fruit: flattened oblong in shape with longitudinal grooves, 144A in color when immature and 201A in color when mature, an average of 5 mm in length and 4 mm in width, seeds were not observed.

It is claimed:

1. A new and distinct cultivar of *Viburnum* plant named 'Bailvibone' as herein illustrated and described.

* * * * *